United States Patent
Lee et al.

(10) Patent No.: US 10,058,316 B2
(45) Date of Patent: Aug. 28, 2018

(54) SURGICAL TRACTION APPARATUS

(71) Applicant: AJOU UNIVERSITY INDUSTRY-ACADEMIC COOPERATION FOUNDATION, Suwon-si, Gyeonggi-do (KR)

(72) Inventors: Moon Gu Lee, Gwacheon-si (KR); Yong Ho Jeon, Suwon-si (KR); Kil Yeon Lee, Seoul (KR); Jae Seung Kim, Suwon-si (KR)

(73) Assignee: AJOU UNIVERSITY INDUSTRY-ACADEMIC COOPERATION FOUNDATION, Suwon-si, Gyeonggi-do (KR)

( * ) Notice: Subject to any disclaimer, the term of this patent is extended or adjusted under 35 U.S.C. 154(b) by 19 days.

(21) Appl. No.: 15/312,291

(22) PCT Filed: May 14, 2015

(86) PCT No.: PCT/KR2015/004868
§ 371 (c)(1),
(2) Date: Nov. 18, 2016

(87) PCT Pub. No.: WO2015/178627
PCT Pub. Date: Nov. 26, 2015

(65) Prior Publication Data
US 2017/0112483 A1    Apr. 27, 2017

(30) Foreign Application Priority Data

May 20, 2014  (KR) .................. 10-2014-0060511

(51) Int. Cl.
*A61B 17/02* (2006.01)
*A61B 17/00* (2006.01)

(52) U.S. Cl.
CPC .............. *A61B 17/0218* (2013.01); *A61B 2017/00876* (2013.01)

(58) Field of Classification Search
CPC . A61B 17/0218; A61B 17/0401; A61B 17/06; A61B 17/122; A61B 17/1285;
(Continued)

(56) References Cited

U.S. PATENT DOCUMENTS

| | | | |
|---|---|---|---|
| 6,459,924 B1 * | 10/2002 | Creighton, IV | A61B 1/00158 128/899 |
| 2009/0043246 A1 * | 2/2009 | Dominguez | A61B 17/0218 604/21 |

FOREIGN PATENT DOCUMENTS

| | | |
|---|---|---|
| JP | 2008259835 A | 10/2008 |
| JP | 2010220876 A | 10/2010 |

(Continued)

*Primary Examiner* — Pedro Philogene
(74) *Attorney, Agent, or Firm* — Vorys, Sater, Seymour & Pease LLP; Mih Suhn Koh (57) ABSTRACT

A surgical traction apparatus according to the present invention includes a moving body portion including a magnetic body and configured to be inserted into a body, a hook portion configured to be connected to the moving body portion inside the body and pull an object inside the body, an operating portion configured to operate the moving body portion to move inside the body while moving outside the body, and a magnet portion configured to be mounted on the operating portion and be with adjustable magnetic strength.

11 Claims, 10 Drawing Sheets

(58) Field of Classification Search
CPC ........ A61B 17/282; A61B 2017/00278; A61B 2017/00411; A61B 2017/00823; A61B 2017/00876; A61B 2017/0474; A61B 2017/2926; A61B 2017/301; A61B 34/70; A61B 34/73; H01F 7/0252
USPC ........... 600/202–210, 427, 114–117; 606/46, 606/129, 144; 604/21
See application file for complete search history.

(56) References Cited

FOREIGN PATENT DOCUMENTS

| KR | 20070000408 U | 4/2007 |
|----|---------------|--------|
| KR | 101293282 B1 | 8/2013 |
| WO | 2008131128 A1 | 10/2008 |

* cited by examiner

SURGICAL TRACTION APPARATUS

TECHNICAL FIELD

The present invention relates to a surgical traction apparatus, and more particularly, to a surgical traction apparatus for remotely pulling organs or tissues inside a body from the body.

BACKGROUND ART

Generally, traditional laparotomy for treating a patient requires a large incision and causes much blood loss during surgery, which slows recovery of the patient after surgery and leaves a big scar, thus negatively affecting the patient's daily life.

To overcome this disadvantage of laparotomy, novel surgical techniques such as minimally invasive surgery (MIS) using a laparoscope have recently been developed.

One example of the related art is disclosed in Korean Utility Model Publication No. 20-2007-0000408 (published on Apr. 6, 2007 and entitled "The structure of Auvard Weighted Speculum adapted LED light with contamination prevention function").

DISCLOSURE OF INVENTION

Technical Problem

The present invention provides a surgical traction apparatus capable of remotely pulling organs or tissues inside a body from the body while adjusting traction as necessary.

Technical Solution

One aspect of the present invention provides a surgical traction apparatus including a moving body portion including a magnetic body and configured to be inserted into a body, a hook portion configured to be connected to the moving body portion inside the body and pull an object inside the body, an operating portion configured to operate the moving body portion to move inside the body while moving outside the body, and a magnet portion configured to be mounted on the operating portion and be with adjustable magnetic strength.

The magnet portion may include a first magnet layer including a permanent magnet having a polarity and a second magnet layer comprising a permanent magnet having a polarity, disposed to be stacked on the first magnet layer, and configured to be changed in relative position with respect to the first magnet layer while changing strength of magnetic force formed with the first magnet layer.

The first magnet layer may have a shape in which permanent magnets having different polarities are alternately arranged, and the second magnet layer may have a shape in which permanent magnets having different polarities are alternately arranged and is movably or rotatably installed above the first magnet layer.

The first magnet layer may include a first circular magnet portion in which permanent magnets having different polarities are alternately arranged to form a circular shape, and the second magnet layer may include a second circular magnet portion in which permanent magnets having different polarities are alternately arranged to form a circular shape and which is changed in relative position with respect to the permanent magnets forming the first circular magnet portion due to rotation and is adjustable in strength of magnetic force formed with the first circular magnet portion.

The magnet portion may include a first case configured to cover the first magnet layer, a second case configured to cover the second magnet layer, be installed to be stacked above the first case, and be rotated, and a bearing installed between the first case and the second case and configured to rotatably support the second case.

The operating portion may include a first base portion in contact with a human body, a first cover portion configured to include an open portion through which the second case is exposed to an outside and be coupled with the first base portion, a first mounting portion formed at the first base portion and on which the first case is detachably mounted, and a fastening portion configured to fasten the second case to the first base portion so that the second case is not separated by a repulsive force between the first magnet layer and the second magnet layer.

The magnet portion may include a permanent magnet portion including a permanent magnet and an electromagnet portion including an electromagnet configured to be with changeable magnetic strength according to a level of a current and be mounted on the operating portion along with the permanent magnet portion.

The electromagnet portion may include a magnetized core portion configured to include a magnetic body and disposed around the permanent magnet portion and a coil portion consecutively wound around the magnetized core portion and configured to magnetize the magnetized core portion when the current flows therethrough.

The magnet portion may further include a wheel operated to rotate, a displacement changing portion configured to convert a rotational displacement of the wheel into an electronic signal, a current adjusting portion configured to receive a signal related to the rotational displacement of the wheel from the displacement changing portion and to adjust a level of the current supplied to the coil portion, and an electromagnet case configured to include a hole portion through which the coil portion passes and to cover the electromagnet portion.

The operating portion may include a second base portion in contact with a human body, a second cover portion configured to include an open portion through which the wheel is exposed to an outside and be coupled with the second base portion, and a second mounting portion formed at the second base portion and on which the electromagnet case is detachably mounted.

The magnet portion may include a magnetically unchangeable portion with a magnetic force of uniformly maintained strength and a magnetically changeable portion configured to be mounted along with the magnetically unchangeable portion on the mounting portion and be with adjustable magnetic strength.

Another aspect of the present invention provides a surgical traction apparatus including a moving body portion including a magnetic body and configured to be inserted into a body, a hook portion configured to be connected to the moving body portion in the body and pull an object in the body, an operating portion configured to operate the moving body portion to move inside the body while outside of the body, and a magnet portion configured to be mounted on the operating portion and be with adjustable magnetic strength. Here, the magnet portion includes a magnetically unchangeable portion configured to include a permanent magnet and a magnetic force of uniformly maintained strength and a magnetically changeable portion configured to include one of a permanent magnet and an electromagnet, be mounted along with the magnetically unchangeable portion on the operating portion, and be with adjustable magnetic strength by moving the permanent magnet or adjusting a level of a current supplied to the electromagnet.

Advantageous Effects

The surgical traction apparatus according to the present invention may adjust traction which pulls organs or tissues inside a body using a moving body portion and a hook portion inserted in the body while an operating portion with a magnet portion configured to be mounted thereon and be with adjustable magnetic strength is moved outside the body.

Accordingly, according to the present invention, when abdominal walls are thin or soft organs or tissues are pulled, the magnetic strength may be adjusted to be low, thereby preventing the organs or tissues from being damaged by the traction.

Also, according to the present invention, when abdominal walls are thick or tough or heavy organs or tissues are pulled, the magnetic strength may be adjusted to stably move or bend organs or tissues to desired positions, thereby smoothly performing a surgery or procedure.

Also, according to the present invention, a permanent magnet provided at the magnet portion may be moved by rotating a part of the magnet portion exposed to the outside of the operating portion or the magnetic strength may be simply adjusted by adjusting a level of current supplied to an electromagnet.

Also, according to the present invention, since the magnetic strength may be continuously adjusted to be increased or decreased in proportion to a rotational displacement of a second case or a wheel, an operator or a clinician may concentrate on a surgery or procedure without being distracted by adjusting the magnetic strength.

BEST MODE FOR INVENTION

Hereinafter, embodiments of a surgical traction apparatus according to the present invention will be described with reference to the attached drawings. Here, thicknesses of lines, sizes of components, or the like shown in the drawings may be exaggerated for clarity and convenience of description.

Also, terms described below are defined considering functions thereof in the present invention, which may vary with intentions of a user and an operator or practice. Accordingly, the definitions of such terms should be understood based on the content throughout the specification.

First, a surgical traction apparatus according to a first embodiment of the present invention will be described.

Figure 1:
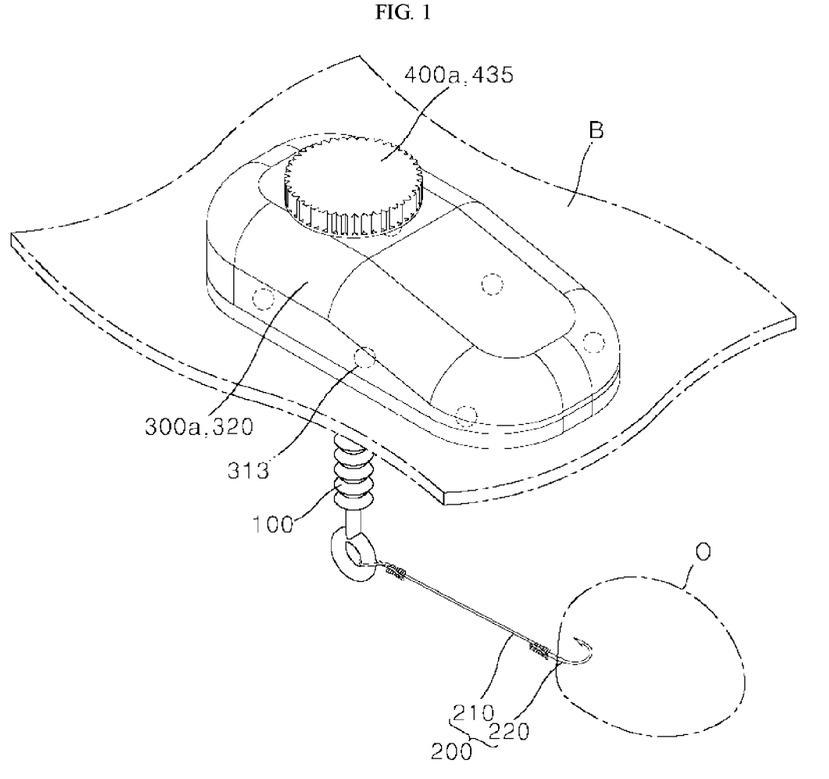
FIG. 1 is a perspective view schematically illustrating a surgical traction apparatus according to a first embodiment of the present invention.
Figure 2:
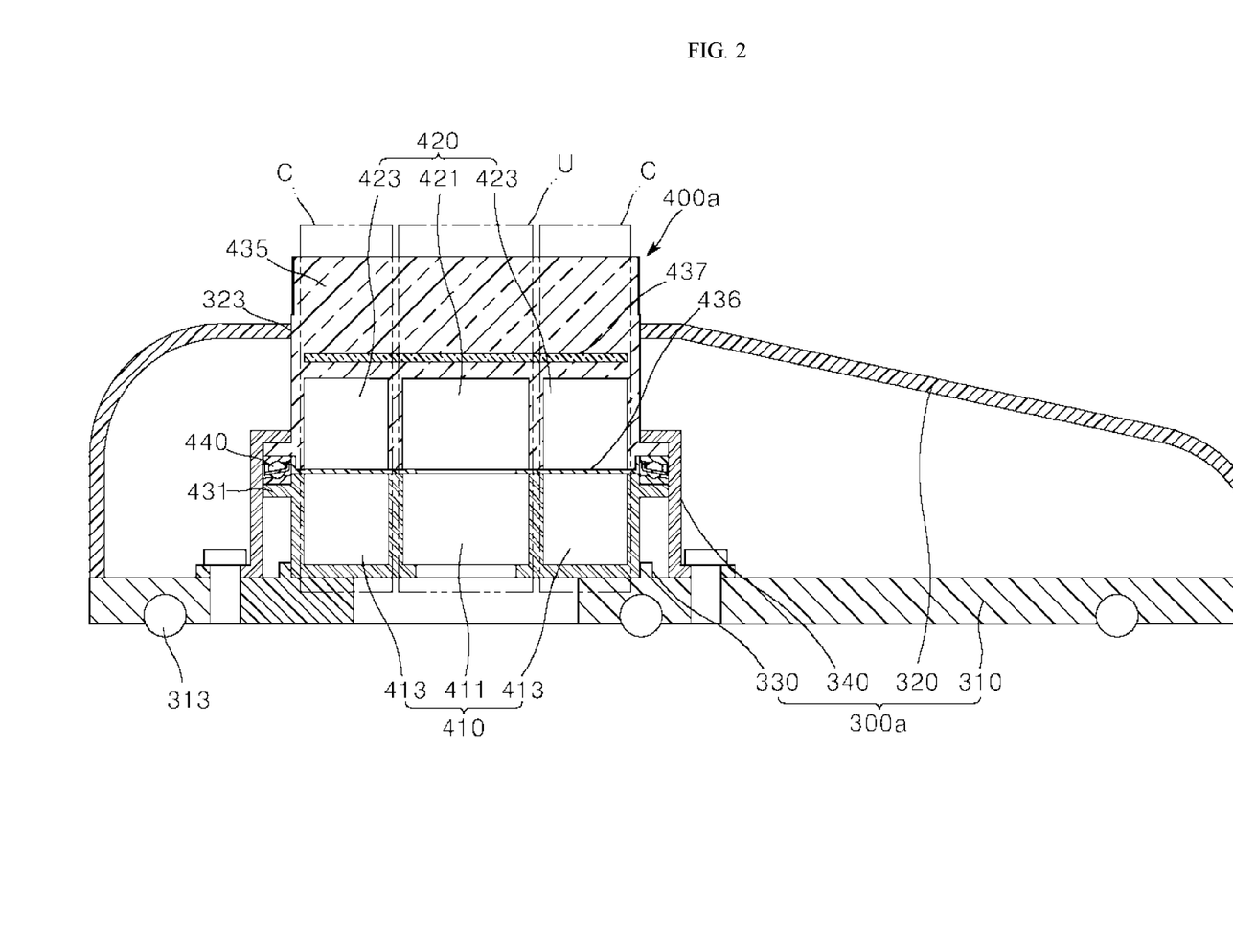
FIG. 2 is a cross-sectional view schematically illustrating an operating portion and a magnet portion according to the first embodiment of the present invention.
Figure 3:
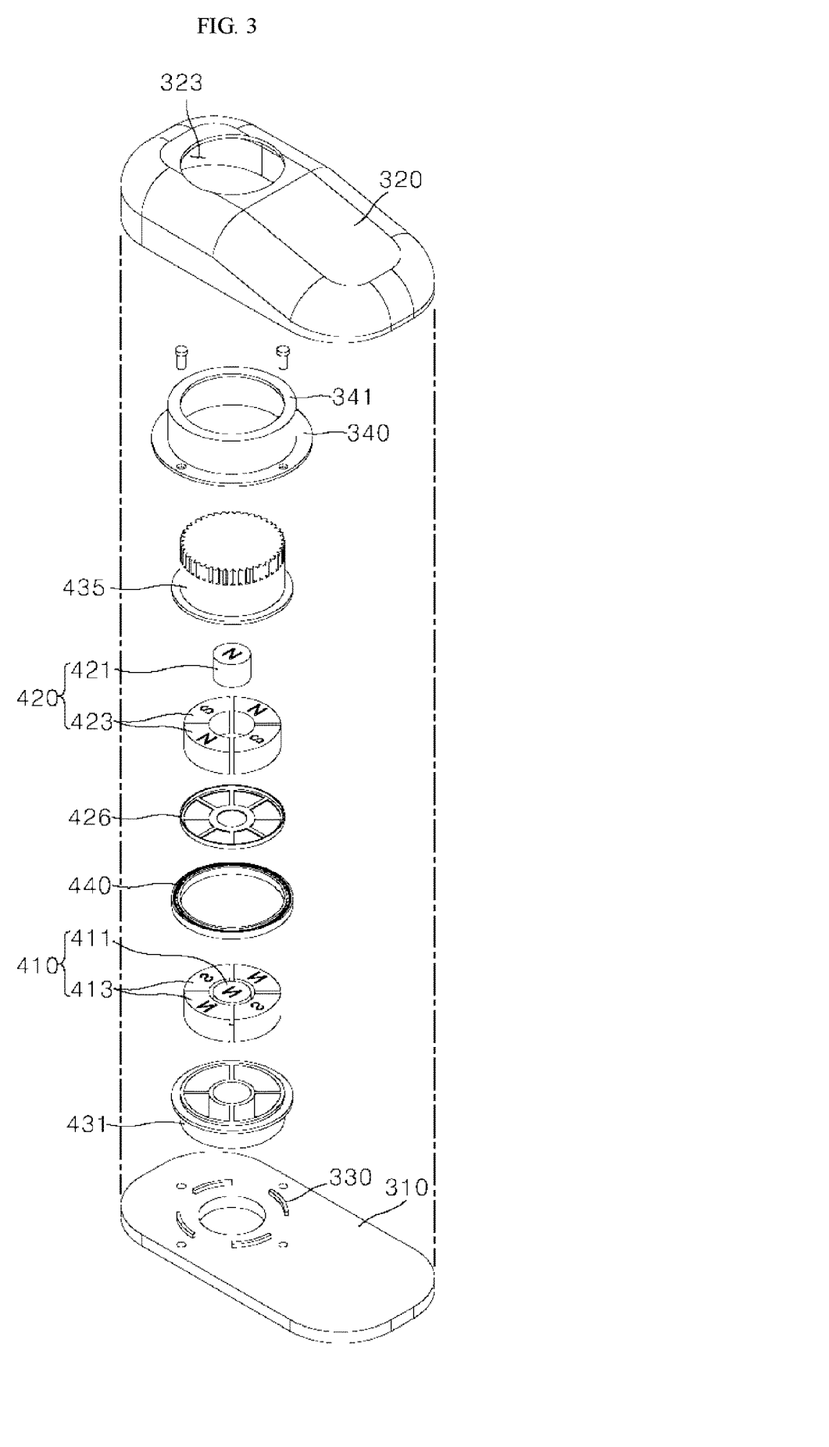
FIG. 3 is an exploded perspective view schematically illustrating the operating portion and the magnet portion according to the first embodiment of the present invention.

FIG. 1 is a perspective view schematically illustrating the surgical traction apparatus according to the first embodiment of the present invention, FIG. 2 is a cross-sectional view schematically illustrating an operating portion and a magnet portion according to the first embodiment of the present invention, and FIG. 3 is an exploded perspective view schematically illustrating the operating portion and the magnet portion according to the first embodiment of the present invention.

Referring to FIGS. 1 to 3, the surgical traction apparatus according to the first embodiment of the present invention includes a moving body portion 100, a hook portion 200, an operating portion 300a, and a magnet portion 400a.

The moving body portion 100 includes a magnetic body attached to a magnet and is inserted into a body. In the description of the present invention, "into a (the) body" refers to into an (the) abdominal wall B. The moving body portion 100 is inserted into the abdominal wall B before a surgical instrument.

The hook portion 200 is connected to the moving body portion 100 in the abdominal wall B and pulls an object O such as an organ or tissue. In detail, the hook portion 200 includes a string portion 210 and a hook 220.

One side of the string portion 210 is connected to the moving body portion 100 and the other side thereof is connected to the hook 220. The string portion 210 includes strings to have infinite degrees of freedom inside the abdominal wall B. Since the string portion 210 has infinite degrees of freedom like this, the object O may be pulled in a desired direction. This acts as a big advantage when securing a space for surgery.

A length of the string portion 210 connected to the moving body portion 100 may be adjustable according to an internal structure of the abdominal wall B and a situation. That is, since the string portion 210 has a configuration in which the one side is connected to the moving body portion 100 and the other side is connected to the hook 220, the length of the string portion 210 may be easily adjusted by changing a portion connected to the moving body portion 100 or the hook 220.

The hook 220 hooks the object O and is connected to the moving body portion 100 through the string portion 210. Accordingly, since tension is formed at the string portion 210 due to movement of the moving body portion 100, the hook 220 is moved in a movement direction of the moving body portion 100 when the string portion 210 is tightly pulled. At the same time, the object O hooked by the hook 220 is pulled and also moves in the movement direction of the moving body portion 100.

The hook 220 is formed in a fish hook shape. Accordingly, an operation of hooking the object O with the hook 220 is easily performed using a gripper and the like inserted into an incised portion, a natural opening portion, or the like The operating portion 300a is a portion configured to operate the movement of the moving body portion 100 inserted in the abdominal wall B from outside of the abdominal wall B and includes the magnet portion 400a configured to form a magnetic force mounted therein. Accordingly, an attractive force is formed between the moving body portion 100 and the operating portion 300a formed including a material attached to the magnet portion 400a so that the moving body portion 100 interworks with movement of the operating portion 300a inside the body and is moved.

Here, since the operating portion 300a should operate the movement of the moving body portion 100 with the abdominal wall B therebetween, it is necessary for an attractive force of a predetermined value or more to be formed between the operating portion 300a and the moving body portion 100. That is, the attractive force between the operating portion 300a and the moving body portion 100 formed by the magnet portion 400a should be of a degree that enables the operating portion 300a to freely move the moving body portion 100 even with the abdominal wall B therebetween.

Simultaneously, the attractive force formed between the operating portion 300a and the moving body portion 100 should be of a degree that does not damage organs or tissues.

The operating portion 300a according to the first embodiment of the present invention includes a first base portion 310, a first cover portion 320, a first mounting portion 330, and a fastening portion 340.

The first base portion 310 is a portion in contact with the abdominal wall B outside the body and forms an exterior of the operating portion 300a along with the first cover portion 320.

A ball portion 313 is installed at one surface of the first base portion 310, more particularly, at a bottom of the first base portion 310, facing the abdominal wall B to be rollable thereon. Accordingly, friction between the first base portion 310 and the abdominal wall B may be reduced. Due to this, the movement of the operating portion 300a in contact with an outer wall of the abdominal wall B that is used may be smoothly performed.

The first cover portion 320 covers the magnet portion 400a to prevent dust, foreign substances, and the like from entering the magnet portion 400a and is coupled with a top of the first base portion 310. An open portion 323 is formed at a top of the first cover portion 320, and a top of the magnet portion 400a is exposed to the outside through the open portion 323.

The first mounting portion 330 on which the magnet portion 400a is detachably mounted is formed at the first base portion 310. The first mounting portion 330 is formed to surround the magnet portion 400a to fix the magnet portion 400a.

A portion of the first base portion 310 positioned inside the first mounting portion 330 is formed to be open downward so that a magnetic force of a first magnet layer 410 and a second magnet layer 420 accommodated in the magnet portion 400a may smoothly reach the abdominal wall B.

The fastening portion 340 fastens the magnet portion 400a to the first base portion 310 to prevent the magnet portion 400a including a permanent magnet from being separated from a position due to a repulsive force between permanent magnets. The fastening portion 340 includes a separation preventing lip portion 341 formed to protrude toward the second magnet layer 420 to prevent an upward separation of the second magnet layer 420 positioned below the magnet portion 400a and is fastened to the first base portion 310 by a fastening member such as a bolt and the like.

The magnet portion 400a has a structure capable of being adjusted magnetic strength outside the operating portion 300a and is detachably mounted on the first mounting portion 330 formed at the first base portion 310. Accordingly, not only fixing a position of the magnet portion 400a but also replacing the magnet portion 400a may be easily performed.

The magnetic strength formed by the magnet portion 400a depends on a thickness of the abdominal wall B or a size or an elastic force of the object O. That is, since the thickness of the abdominal wall B and the size and elastic force of the object O are different for each person or surgery portion, it is necessary to adjust the magnetic strength formed by the magnet portion 400a to form an adequate attractive force between the magnet portion 400a and the moving body portion 100.

The magnet portion 400a according to the first embodiment of the present invention includes the first magnet layer 410, the second magnet layer 420, a first case 431, a second case 435, and a bearing 440.

The magnet portion 400a has a structure in which the first magnet layer 410 and the second magnet layer 420 are stacked, and each of the first magnet layer 410 and the second magnet layer 420 includes a plurality of permanent magnets having the same polarity.

The second magnet layer 420 is moved or rotated by an operation of a user performed outside of the operating portion 300a while being stacked above the first magnet layer 410. Due to the movement or rotation of the second magnet layer 420 as described above, a relative position thereof with respect to the first magnet layer 410 changes, thereby changing strength of a magnetic force formed with the first magnet layer 410.

For example, when the second magnet layer 420 is gradually moved while an N pole of the permanent magnets provided at the first magnet layer 410 and an S pole of the permanent magnets provided at the second magnet layer 420 face each other, an area in which the N pole faces the S pole is gradually reduced. In such a process as described above, a shape of a magnetic force line and strength of a magnetic force formed by the permanent magnets provided at the first magnet layer 410 and the permanent magnets provided at the second magnet layer 420 are changed.

Meanwhile, the change of the relative position of the second magnet layer 420 with respect to the first magnet layer 410 due to the movement or rotation refers to a change of positions of the permanent magnets provided at the second magnet layer 420 based on positions of the permanent magnets provided at the first magnet layer 410 while the second magnet layer 420 moves in a horizontal direction or a vertical direction or rotates at a position.

The first magnet layer 410 includes a first central magnet portion 411 positioned at a central portion thereof and a first circular magnet portion 413 formed around the first central magnet portion 411, and is covered by the first case 431.

The first central magnet portion 411 is formed with permanent magnets. The first circular magnet portion 413 has a structure in which permanent magnets having different polarities are alternately arranged in a circular shape.

Like the first magnet layer 410, the second magnet layer 420 includes a second central magnet portion 421 positioned at a central portion thereof and a second circular magnet portion 423 formed around the second central magnet portion 421, and is covered by the second case 435.

The second central magnet portion 421 includes permanent magnets that are installed to face the first central magnet portion 411 in groups of different polarities. The second circular magnet portion 423 has the same structure as the first circular magnet portion 413 in which permanent magnets having different polarities form a circular shape.

Accordingly, when the second circular magnet portion 423 is rotated, relative positions of the first circular magnet portion 413 and the second circular magnet portion 423 are changed. Here, the first magnet layer 410 is maintained in a state of being fixed to the first base portion 310 by the first mounting portion 330, and the rotation of the second circular magnet portion 423 is performed by rotating the second case 435 exposed to the outside through the open portion 323 formed by the first cover portion 320.

The first case 431 covers the first magnet layer 410. The first case 431 includes a plurality of partition walls configured to form a space portion radially divided based on a central portion thereof so that the first central magnet portion 411 and the first circular magnet portion 413 may be accommodated at a place without interfering with each other.

The second case 435 is installed to cover the second magnet layer 420 and to be stacked on the first case 431. Like the first case 431, the second case 435 includes a plurality of partition walls configured to form a space portion radially divided based on a central portion thereof so that the second central magnet portion 421 and the second circular magnet portion 423 may be accommodated at a place without interfering with each other.

The bearing 440 configured to rotatably support the second case 435 is installed between the first case 431 and the second case 435. Since the bearing 440 is not limited to a particular structure or shape including an example in which only a rolling ball is included therein and another example a ring-shaped contact portion in contact with each of the first case 431 and the second case 435 is included as long as the bearing 440 rotatably supports the second case 435, and a detailed description thereof will be omitted. The second case 435 may be stably rotated by the bearing 440 at a position by a rotating operation of the user without interfering with the first case 431.

Also, a supporting plate 436 configured to support the second magnet layer 420 at a bottom end thereof is installed below the second case 435 and prevents the second magnet layer 420 from being moved downward by the attractive force of the first magnet layer 410.

Also, a magnetic shielding member 437 including a metal material and the like is installed above the second magnet layer 420 in the second case 435 to reduce a magnetic force of the second magnet layer 420 that acts outside of a top of the operating portion 300a. Since the magnetic force acting outside of the top of the operating portion 300a may be reduced using the magnetic shielding member 437, inconvenience caused by a magnetic force acting on surgical instruments and the like formed of metal materials may be prevented.

FIGS. 4A to 4D are conceptual views illustrating a method of adjusting magnetic strength using the magnet portion according to the first embodiment of the present invention.

Figure 4A:
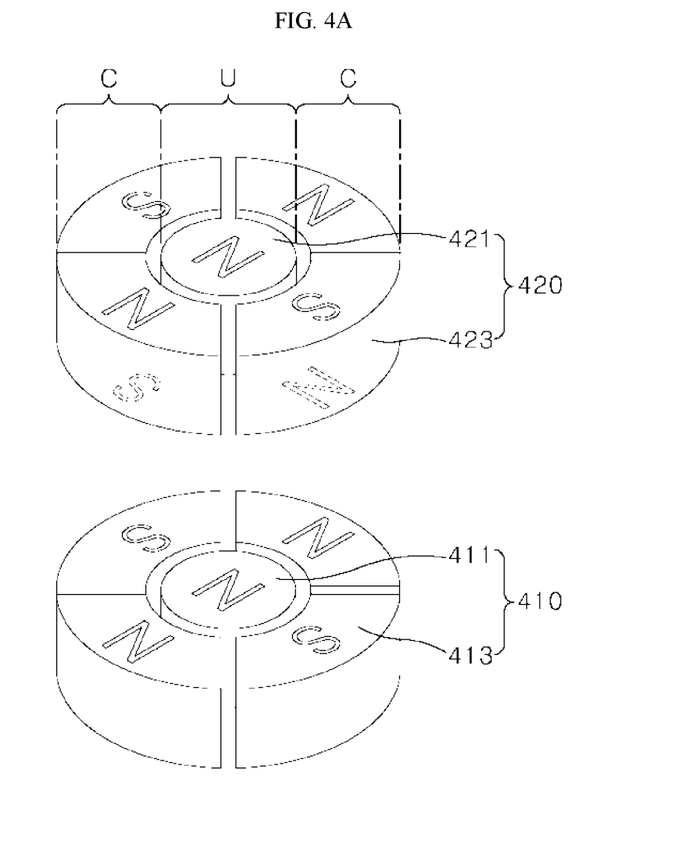
FIGS. 4A to 4D are conceptual views illustrating a method of operating magnetic strength using the magnet portion according to the first embodiment of the present invention.
Figure 4B:
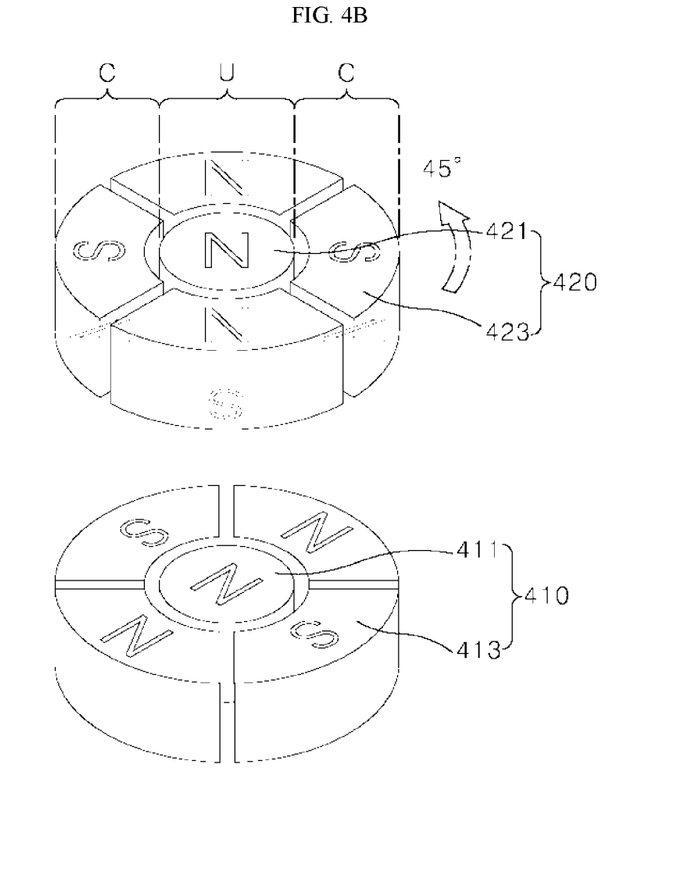
Figure 4C:
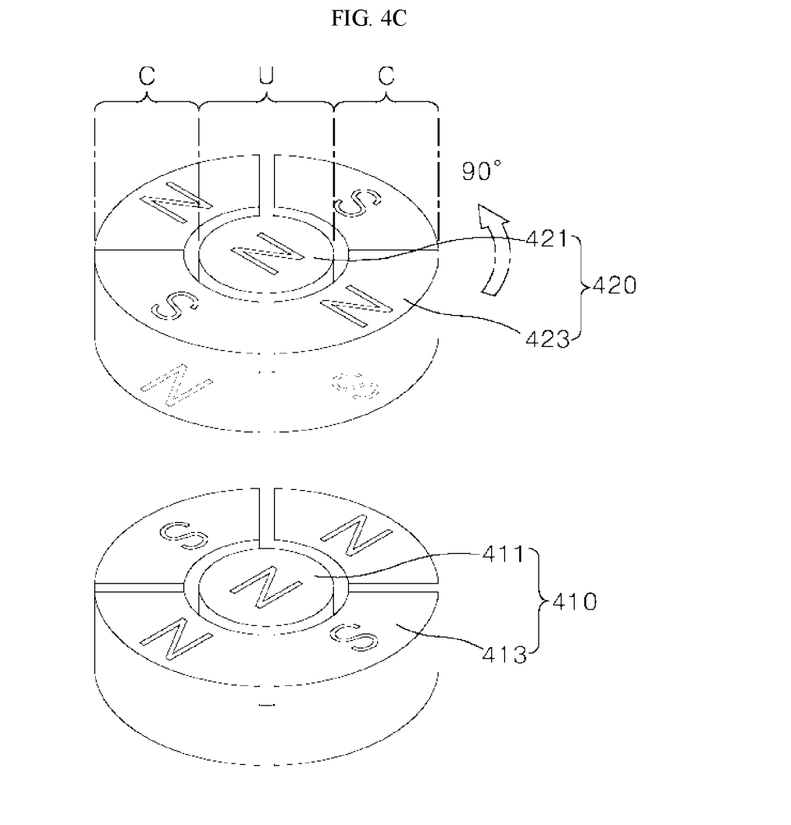
Figure 4D:
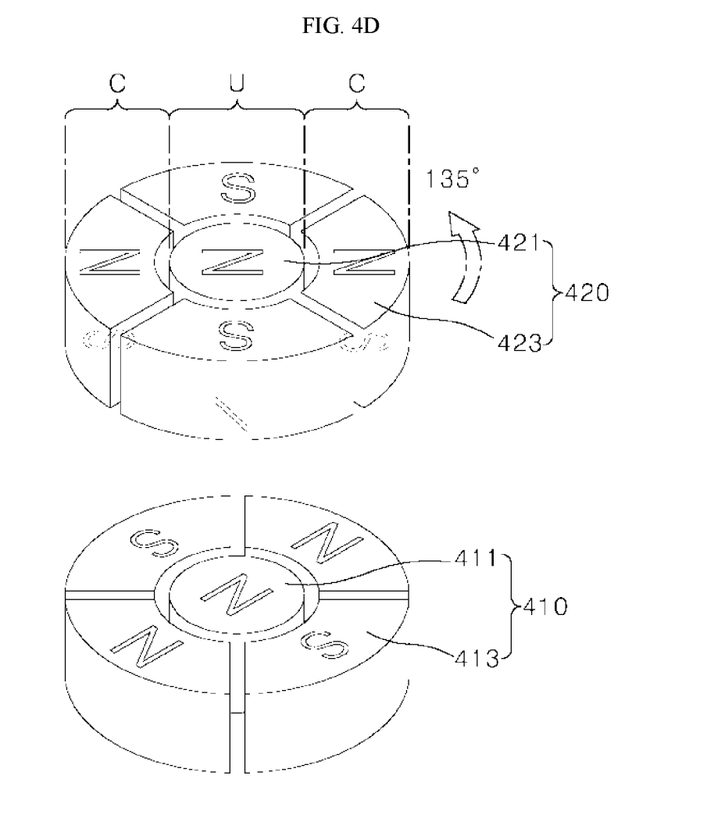

When the second magnet layer 420 is rotated at a place in a state in which the permanent magnets provided at each of the first circular magnet portion 413 and the second circular magnet portion 423 face each other with different polarities as shown in FIG. 4A, an area in which the same magnetic forces face each other is gradually enlarged as shown in FIGS. 4B and 4C or an area in which different polarities face each other is gradually enlarged as shown in FIG. 4D.

When the second magnet layer 420 is rotated, as relative positions of the permanent magnets forming the first circular magnet portion 413 and the permanent magnets forming the second circular magnet portion 423 are gradually changed, the strength of magnetic force formed by the first circular magnet portion 413 and the second circular magnet portion 423 varies with a uniform pattern.

When the permanent magnets provided at each of the first circular magnet portion 413 and the second circular magnet portion 423 face each other with different polarities as shown in FIG. 4A and the highest magnetic strength acts on the bottom of the operating portion 300a, the magnetic strength acting on the bottom of the operating portion 300a may be gradually adjusted to be low through a process shown in FIG. 4B or 4D when operated so that the same polarities face each other as shown in FIG. 4C. Here, a central portion of the magnet portion 400a at which the first central magnet portion 411 and the second central magnet portion 421 are positioned maintains a uniform magnetic force.

The magnet portion 400a according to the first embodiment configured to act as described above includes a structure in which a magnetically unchangeable portion U with a uniform magnetic strength is formed at the central portion thereof and a magnetically changeable portion C with an adjustable magnetic strength is formed at a peripheral portion of the central portion thereof.

While a minimal magnetic force necessary for pulling organs or tissues is not lost and is uniformly maintained by the magnetically unchangeable portion U formed by the first central magnet portion 411 and the second central magnet portion 421, strength of an additionally acting magnetic force may be adjusted to be increased or decreased using the magnetically changeable portion C formed by the first circular magnet portion 413 and the second circular magnet portion 423.

Accordingly, traction may be stably adjusted to be increased or decreased within a range that does not damage organs or tissues while a state of forming an attractive force with a predetermined value that moves the moving body portion 100 is stably maintained.

One hook portion 200 has been described as being connected to the moving body portion 100 in the first embodiment of the present invention as an example, but the present invention is not limited thereto. Accordingly, a plurality of such hook portions 200 may be simultaneously connected to the moving body portion 100. In this case, since traction is distributed to the plurality of hook portions 200, the object O may be more easily pulled.

As described above, since an organ or tissue in a body is pulled by the hook portion inserted before surgical instruments in the surgical traction apparatus according to the present invention, an additional incision for pulling the organ or tissue is not necessary.

Also, since the surgical traction apparatus according to the present invention is able to remotely pull the object O in the body, an organ or tissue may be easily accessed and a clear view for a surgery may be provided.

Also, while the strength of a magnetic force formed by the magnet portion 400a is adjusted as described above, the traction which pulls the object O may be adjusted using the moving body portion 100 and the hook portion 200 inserted in the body.

Accordingly, when the abdominal wall B is thin or the object O which is soft is pulled, magnetic strength is adjusted to be low so that the object O may be prevented from being damaged by traction.

Also, when the abdominal wall is thick or the object O which is tough or heavy is pulled, the magnetic strength is adjusted to stably move or bend the object O to a desired position so that a surgery or procedure may be smoothly performed.

Also, the magnetic strength may be simply adjusted by rotating a part of the second case 435 exposed to the outside of the operating portion 300a to move the permanent magnets provided at the second magnet layer 420.

Also, since a simple control method of continuously adjusting the magnetic strength to be increased or decreased in proportion to a rotational displacement of the second case 435 and the second magnet layer 420 is implemented, an operator or a clinician may concentrate on a surgery or procedure without being distracted by adjusting the magnetic strength.

Next, a surgical traction apparatus according to a second embodiment of the present invention will be described.

Hereinafter, in the description of the surgical traction apparatus according to the second embodiment of the present invention, a detailed description that overlaps with the content of the surgical traction apparatus according to the first embodiment of the present invention which has been described with reference to FIGS. 1 to 4D will be omitted.

Figure 5:
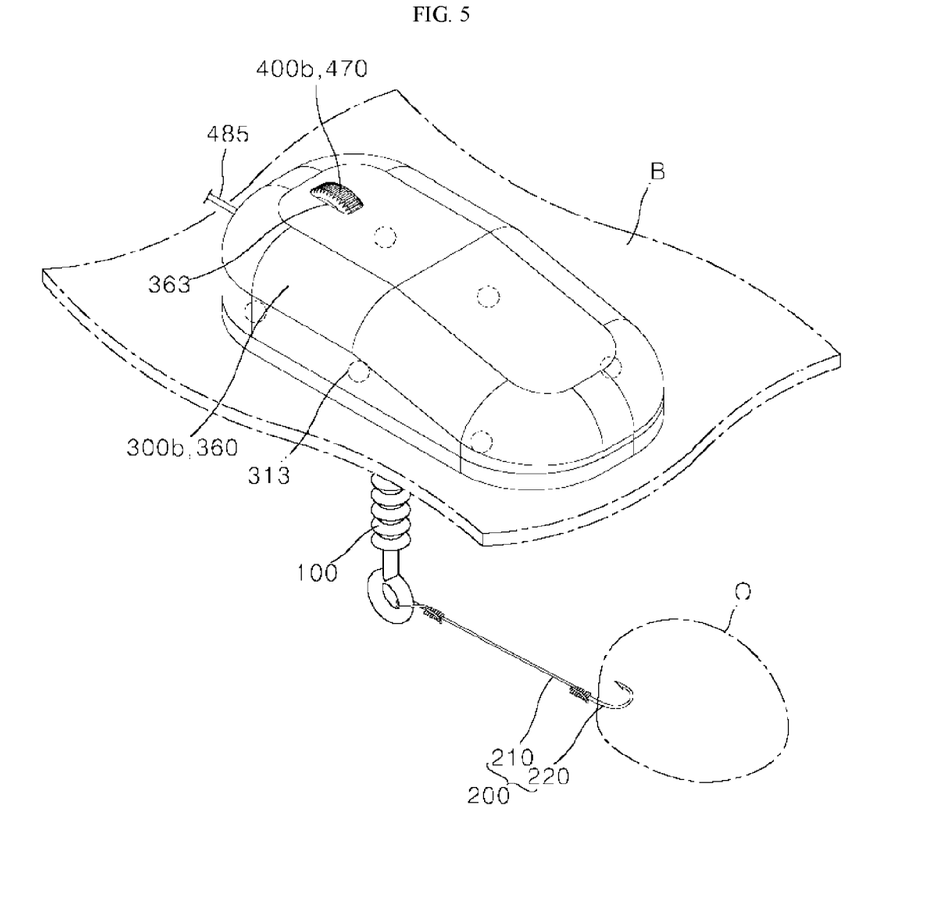
FIG. 5 is a perspective view schematically illustrating a surgical traction apparatus according to a second embodiment of the present invention.
Figure 6:
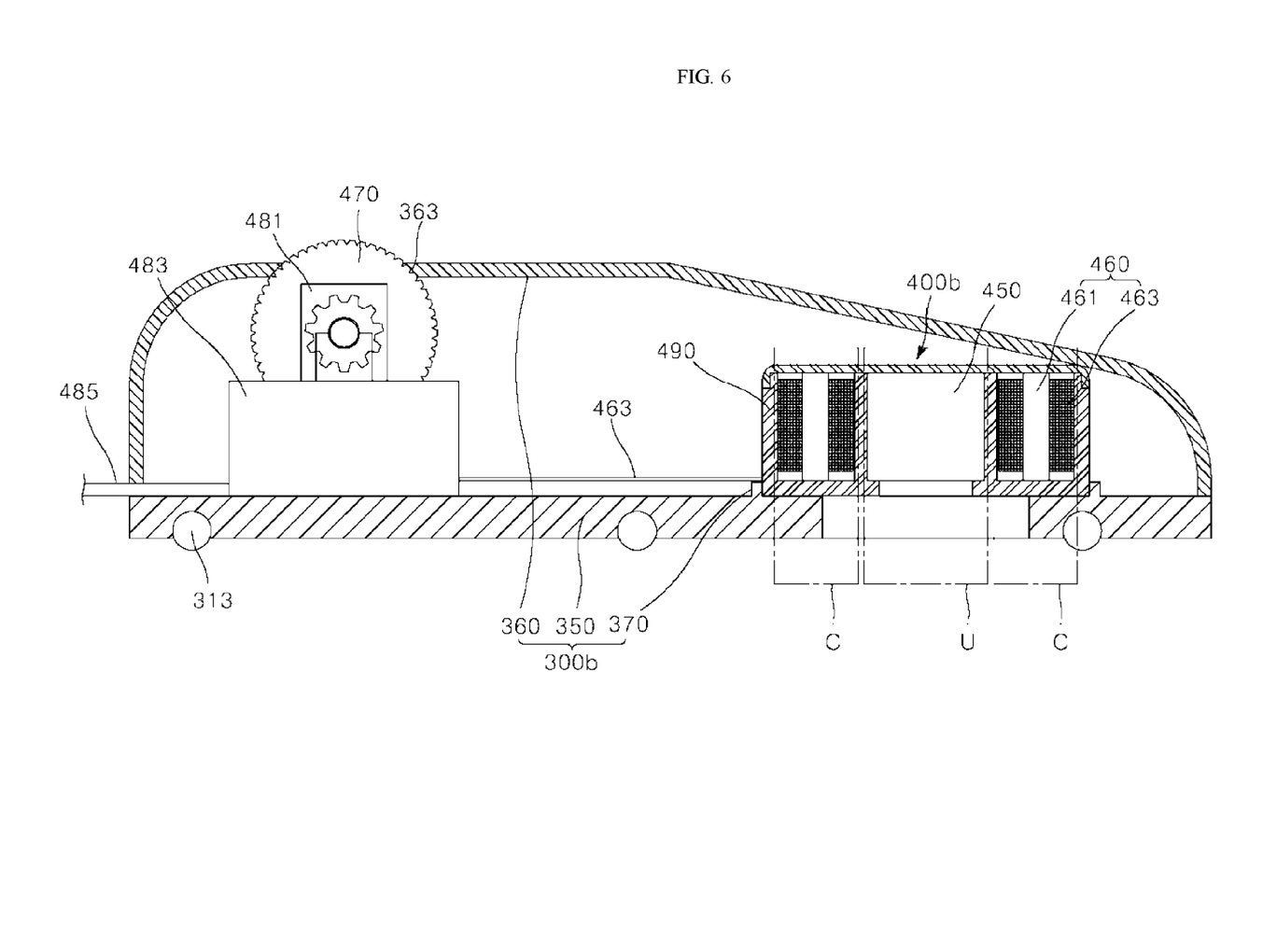
FIG. 6 is a cross-sectional view schematically illustrating an operating portion and a magnet portion according to the second embodiment of the present invention.
Figure 7:
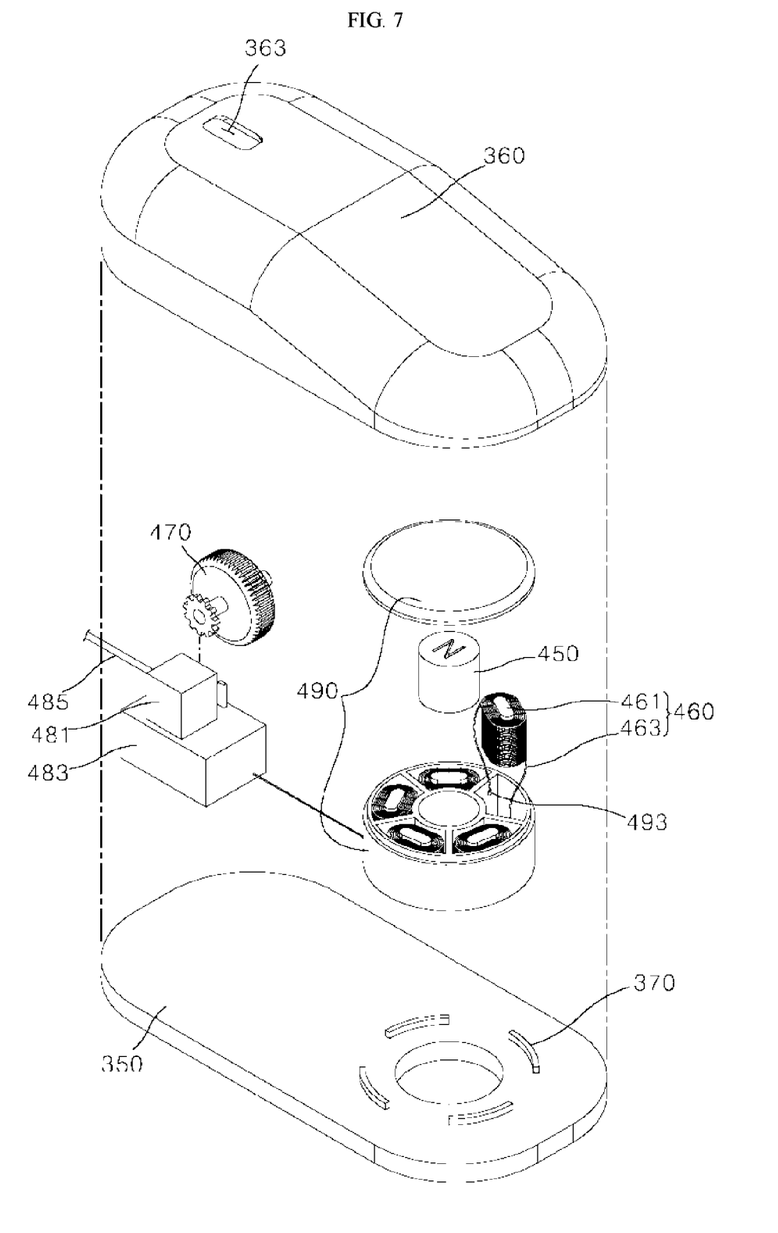
FIG. 7 is an exploded perspective view schematically illustrating the operating portion and the magnet portion according to the second embodiment of the present invention.

FIG. 5 is a perspective view schematically illustrating the surgical traction apparatus according to the second embodiment of the present invention, FIG. 6 is a cross-sectional view schematically illustrating an operating portion and a magnet portion according to the second embodiment of the present invention, and FIG. 7 is an exploded perspective view schematically illustrating the operating portion and the magnet portion according to the second embodiment of the present invention.

Referring to FIGS. 5 to 7, an operating portion 300b according to the second embodiment of the present invention includes a second base portion 350, a second cover portion 360, and a second mounting portion 370.

The second base portion 350 is a portion in contact with the abdominal wall B outside a body and forms an exterior of the operating portion 300b along with the second cover portion 360.

The ball portion 313 is installed at one surface of the second base portion 350, more particularly, at a bottom portion of the second base portion 350, facing the abdominal wall B to be rollable thereon. Accordingly, friction between the second base portion 350 and the abdominal wall B may be reduced. Due to this, the movement of the operating portion 300b used in contact with an outer wall of the abdominal wall B may be smoothly performed.

The second cover portion 360 covers a magnet portion 400b to prevent dust, foreign substances, and the like from entering the magnet portion 400b and is coupled with a top of the second base portion 350. An open portion 363 is formed at a top of the second cover portion 360, and a top of the magnet portion 400b is exposed to the outside through the open portion 363.

The second mounting portion 370 on which an electromagnet case 490 is detachably mounted is formed at the second base portion 350. The second mounting portion 370 is formed to surround the electromagnet case 490 to fix the electromagnet case 490.

A portion of the second base portion 350 positioned inside the second mounting portion 370 is formed to be open downward so that a magnetic force of a permanent magnet portion 450 and an electromagnet portion 460 accommodated in the electromagnet case 490 may smoothly reach the abdominal wall B.

The magnet portion 400b according to the second embodiment of the present invention includes the permanent magnet portion 450, the electromagnet portion 460, a wheel 470, a displacement changing portion 481, a current adjusting portion 483, and the electromagnet case 490.

The permanent magnet portion 450 includes a permanent magnet maintaining a uniform magnetic force.

The electromagnet portion 460 includes an electromagnet with a magnetic force of changeable strength according to a level of a current and is disposed around the permanent magnet portion 450.

The electromagnet portion 460 according to the second embodiment of the present invention includes a magnetized core portion 461 and a coil portion 463.

The magnetized core portion 461 includes a magnetic body, and a plurality of such magnetized core portions 461 are arranged around the permanent magnet portion 450 at regular intervals.

The coil portion 463 is consecutively wound around the plurality of magnetized core portions 461. When a current flows through the coil portion 463, the magnetized core portion 461 are magnetized and form a magnetic force, and strength of the magnetic force increases in proportion to strength of the current flowing through the coil portion 463.

The wheel 470 has a rotatable structure and is installed to be exposed to the outside of the operating portion 300b through the open portion 363 formed at the second cover portion 360. The wheel 470 is rotated by a simple rotating operation in which a finger in contact with a top of the wheel 470 exposed to the outside of the operating portion 300b pushes or pulls the wheel 470.

The displacement changing portion 481 converts a rotational displacement of the wheel 470 into an electronic signal. The displacement changing portion 481 is an apparatus configured to convert a physical quantity which is a mechanical displacement of the wheel 470 into an electronic signal and may include an encoder and the like.

The current adjusting portion 483 includes a current adjusting circuit capable of adjusting a level of a current supplied from the outside of the operating portion 300b through a current supply line 485 to be increased or decreased and is connected to the displacement changing portion 481. The current adjusting portion 483 receives a signal related to the rotational displacement of the wheel 470 from the displacement changing portion 481, adjusts a level of the current supplied through the current supply line 485 to be increased or decreased, and transfers the current to the coil portion 463.

The level of the current supplied to the coil portion 463 may be gradually increased or decreased in proportion to the rotational displacement of the wheel 470 while the wheel 470 is rotated using the displacement changing portion 481 and the current adjusting portion 483 performing the functions described above.

The electromagnet case 490 is a portion which covers the electromagnet portion 460 and includes a plurality of partition walls forming a space portion radially divided based on a central portion thereof to accommodate the permanent magnet portion 450 and the electromagnet portion 460 at a place without interfering with each other. The permanent magnet portion 450 is accommodated in the central portion of the electromagnet case 490, and a plurality of electromagnet portions 460 are accommodated in a peripheral portion of the electromagnet case 490.

A hole portion 493 through which the coil portion 463 may consecutively pass through the partition walls is formed at the electromagnet case 490 so that the plurality of magnetized core portions 461 may be simultaneously magnetized to have the same strength using one coil portion 463.

In the magnet portion 400b according to the second embodiment of the present invention, the permanent magnet portion 450 and the electromagnet portion 460 form the magnetically unchangeable portion U maintained with the uniform magnetic strength and the magnetically changeable portion C with an adjustable magnetic strength, respectively.

The strength of the additionally acting magnetic force may be adjusted to be increased or decreased using the magnetically changeable portion C formed by the electromagnet portion 460 while a minimal magnetic force necessary for pulling the object O is uniformly maintained.

Accordingly, like the surgical traction apparatus according to the first embodiment of the present invention, the attractive force may be stably adjusted to be increased or decreased within a range that does not damage the object O while a state in which an attractive force with a predetermined value which moves the moving body portion 100 is formed is stably maintained.

According to the surgical traction apparatus according to the second embodiment of the present invention, the traction which pulls the object O may be adjusted using the moving body portion 100 and the hook portion 200 inserted in the body while adjusting the strength of the magnetic force formed by the electromagnet portion 460 as described above.

Also, the level of the current supplied to the electromagnet portion 460 may be changed and the magnetic strength may be simply adjusted by rotating a part of the wheel 470 exposed to the outside of the operating portion 300b.

Also, since a simple control method of continuously adjusting the magnetic strength to be increased or decreased in proportion to the rotational displacement of the wheel 470 is implemented, an operator or a clinician may concentrate on a surgery or procedure without being distracted by adjusting the magnetic strength.

Although the present invention has been described with reference to the embodiments shown in the drawings, it should be understood that the embodiments are merely examples and various modifications and equivalents thereof may be made by one of ordinary skill in the art. Accordingly, the technical scope of the present invention should be defined by the following claims.

The invention claimed is:

1. A surgical traction apparatus comprising:
   a moving body portion including a magnetic body and configured to be inserted into a body;
   a hook portion configured to be connected to the moving body portion inside the body and pull an object inside the body;
   an operating portion configured to operate the moving body portion to move inside the body while moving outside the body; and
   a magnet portion configured to be mounted on the operating portion and be with adjustable magnetic strength,
   wherein the magnet portion comprises:
   a first magnet layer comprising a permanent magnet having a polarity; and
   a second magnet layer comprising a permanent magnet having a polarity, disposed to be stacked on the first magnet layer, and configured to be changed in relative position with respect to the first magnet layer while changing strength of a magnetic force formed with the first magnet layer.

2. The surgical traction apparatus of claim 1, wherein the first magnet layer has a shape in which permanent magnets having different polarities are alternately arranged, and wherein the second magnet layer has a shape in which permanent magnets having different polarities are alternately arranged and is movably or rotatably installed above the first magnet layer.

3. The surgical traction apparatus of claim 1, wherein the first magnet layer comprises a first circular magnet portion in which permanent magnets having different polarities are alternately arranged to form a circular shape, and
   wherein the second magnet layer comprises a second circular magnet portion in which permanent magnets having different polarities are alternately arranged to form a circular shape and which is changed in relative position with respect to the permanent magnets forming the first circular magnet portion due to rotation and is adjustable in strength of the magnetic force formed with the first circular magnet portion.

4. The surgical traction apparatus of claim 3, wherein the magnet portion comprises:
   a first case configured to cover the first magnet layer;
   a second case configured to cover the second magnet layer, be installed to be stacked above the first case, and be rotated; and
   a bearing installed between the first case and the second case and configured to rotatably support the second case.

5. The surgical traction apparatus of claim 4, wherein the operating portion comprises:
   a first base portion in contact with the body;
   a first cover portion configured to include an open portion through which the second case is exposed to an outside and be coupled with the first base portion;
   a first mounting portion formed at the first base portion and on which the first case is detachably mounted; and
   a fastening portion configured to fasten the second case to the first base portion so that the second case is not separated by a repulsive force between the first magnet layer and the second magnet layer.

6. A surgical traction apparatus comprising:
   a moving body portion including a magnetic body and configured to be inserted into a body;
   a hook portion configured to be connected to the moving body portion inside the body and pull an object inside the body;
   an operating portion configured to operate the moving body portion to move inside the body while moving outside the body; and
   a magnet portion configured to be mounted on the operating portion and be with adjustable magnetic strength,
   wherein the magnet portion comprises:
   a permanent magnet portion comprising a permanent magnet; and
   an electromagnet portion comprising an electromagnet configured to be with changeable magnetic strength according to a level of a current and be mounted on the operating portion along with the permanent magnet portion.

7. The surgical traction apparatus of claim 6, wherein the electromagnet portion comprises:
   a magnetized core portion configured to include a magnetic body and disposed around the permanent magnet portion; and
   a coil portion consecutively wound around the magnetized core portion and configured to magnetize the magnetized core portion when the current flows therethrough.

8. The surgical traction apparatus of claim 7, wherein the magnet portion further comprises:

a wheel operated to rotate;

a displacement changing portion configured to convert a rotational displacement of the wheel into an electronic signal;

a current adjusting portion configured to receive a signal related to the rotational displacement of the wheel from the displacement changing portion and to adjust a level of the current supplied to the coil portion; and an electromagnet case configured to include a hole portion through which the coil portion passes and to cover the electromagnet portion.

9. The surgical traction apparatus of claim 8, wherein the operating portion comprises:

a second base portion in contact with the body;

a second cover portion configured to include an open portion through which the wheel is exposed to an outside and be coupled with the second base portion; and a second mounting portion formed at the second base portion and on which the electromagnet case is detachably mounted.

10. A surgical traction apparatus comprising:

a moving body portion including a magnetic body and configured to be inserted into a body;

a hook portion configured to be connected to the moving body portion inside the body and pull an object inside the body;

an operating portion configured to operate the moving body portion to move inside the body while moving outside the body; and a magnet portion configured to be mounted on the operating portion and be with adjustable magnetic strength, wherein the magnet portion comprises:

a magnetically unchangeable portion with a magnetic force of uniformly maintained strength; and a magnetically changeable portion configured to be mounted along with the magnetically unchangeable portion on the mounting portion and be with adjustable magnetic strength.

11. A surgical traction apparatus comprising:

a moving body portion including a magnetic body and configured to be inserted into a body;

a hook portion configured to be connected to the moving body portion in the body and pull an object in the body;

an operating portion configured to operate the moving body portion to move inside the body while outside of the body; and a magnet portion configured to be mounted on the operating portion and be with adjustable magnetic strength, wherein the magnet portion comprises:

a magnetically unchangeable portion configured to include a permanent magnet with a magnetic force of uniformly maintained strength; and a magnetically changeable portion configured to include one of a permanent magnet and an electromagnet, be mounted along with the magnetically unchangeable portion on the operating portion, and be with adjustable magnetic strength by moving the permanent magnet or adjusting a level of a current supplied to the electromagnet.

* * * * *